(12) United States Patent
Jakoby et al.

(10) Patent No.: US 6,786,080 B2
(45) Date of Patent: Sep. 7, 2004

(54) METHOD FOR ASSESSING THE DETERIORATION OF MOTOR OIL

(75) Inventors: Bernhard Jakoby, Vienna (AT); Stephan Buch, Weil der Stadt (DE); Oliver Schatz, Reutlingen (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 10/204,762

(22) PCT Filed: Feb. 7, 2001

(86) PCT No.: PCT/DE01/00460
§ 371 (c)(1),
(2), (4) Date: Dec. 20, 2002

(87) PCT Pub. No.: WO01/63101
PCT Pub. Date: Aug. 30, 2001

(65) Prior Publication Data
US 2003/0150256 A1 Aug. 14, 2003

(30) Foreign Application Priority Data
Feb. 24, 2000 (DE) ........................ 100 08 547

(51) Int. Cl.$^7$ .............................................. G01N 33/26
(52) U.S. Cl. .................... 73/54.01; 73/54.02; 73/54.42; 73/54.43
(58) Field of Search ....................... 73/10, 53.05, 54.01, 73/54.02, 54.42, 54.43

(56) References Cited

U.S. PATENT DOCUMENTS

| | | | | |
|---|---|---|---|---|
| 3,829,217 A | * | 8/1974 | Johnson et al. ............... 356/70 |
| 4,007,629 A | * | 2/1977 | Hochstein ................... 73/53.05 |
| 4,029,554 A | * | 6/1977 | Ellison ...................... 205/794.5 |
| 4,306,525 A | * | 12/1981 | Faxvog ................... 123/196 S |
| 4,497,200 A | * | 2/1985 | Tournier ..................... 73/53.05 |
| 4,506,337 A | * | 3/1985 | Yasuhara ....................... 701/30 |
| 4,646,070 A | * | 2/1987 | Yasuhara et al. ............. 340/603 |
| 4,675,662 A | * | 6/1987 | Kondo et al. ................ 340/631 |
| 4,677,847 A | * | 7/1987 | Sawatari et al. ............. 73/53.05 |
| 4,694,793 A | * | 9/1987 | Kawakita et al. ......... 123/196 S |
| 4,733,556 A | * | 3/1988 | Meitzler et al. ............. 73/53.05 |
| 4,785,287 A | * | 11/1988 | Honma et al. .............. 340/631 |
| 4,796,204 A | * | 1/1989 | Inoue ..................... 123/196 S |
| 4,839,831 A | * | 6/1989 | Imajo et al. ................ 73/53.05 |
| 4,847,768 A | * | 7/1989 | Schwartz et al. ............. 701/30 |
| 5,049,742 A | * | 9/1991 | Hosonuma et al. .......... 250/301 |
| 5,060,156 A | * | 10/1991 | Vajgart et al. ................. 701/30 |
| 5,159,313 A | * | 10/1992 | Kawai et al. ............. 340/450.3 |
| 5,320,761 A | | 6/1994 | Hoult et al. .................... 252/9 |
| 5,377,531 A | * | 1/1995 | Gomm ....................... 73/53.05 |
| 5,604,441 A | * | 2/1997 | Freese, V et al. ........... 324/663 |
| 5,750,887 A | * | 5/1998 | Schricker ................... 73/117.3 |
| 5,964,318 A | * | 10/1999 | Boyle et al. ................. 184/1.5 |
| 6,023,961 A | * | 2/2000 | Discenzo et al. ........... 73/54.01 |
| 6,196,057 B1 | * | 3/2001 | Discenzo ................... 73/54.01 |

FOREIGN PATENT DOCUMENTS

| | | |
|---|---|---|
| WO | WO 99 24699 | 5/1999 |
| WO | WO 99 31478 | 6/1999 |

\* cited by examiner

*Primary Examiner*—Hezron Williams
*Assistant Examiner*—David A. Rogers
(74) *Attorney, Agent, or Firm*—Kenyon & Kenyon

(57) ABSTRACT

A method for assessing the deterioration of motor oil is provided, in which the oil viscosity of the motor oil is measured by a sensor, and the length of an oil-change interval is determined in an evaluating electronics having a display device. According to the present invention, it is provided that a temperature sensor for the simultaneous determination of the oil temperature is assigned to the sensor for measuring the oil viscosity, and the oil viscosity and oil temperature are measured in the cooling phase of the engine after it has been switched off.

15 Claims, No Drawings

METHOD FOR ASSESSING THE DETERIORATION OF MOTOR OIL

FIELD OF THE INVENTION

The present invention relates to a method for assessing the deterioration of motor oil.

BACKGROUND INFORMATION

Software-based systems for indicating the necessity of an oil change in motor vehicles are conventional. Some of these systems are based on algorithms which evaluate parameters such as the kilometers driven since the last oil change or the frequency of cold starts.

Alternative conventional methods use sensor signals which directly describe the physical condition of the oil. Appropriate sensors may measure, for example, the dielectric constant of the oil or the oil viscosity. In this context, a viscosity-based oil-change criterion may be derived from the determination of the viscosity change in the motor oil since the last oil change, since motor oil deterioration may be associated with an increase in the viscosity value. An evaluating electronics having an associated display device may store, for example, a viscosity threshold value, which is compared with the measured viscosity values of the motor oil. The vehicle driver may be provided with an indication regarding the impending necessity for the next oil change when the viscosity threshold value is exceeded.

The physical oil parameters measured using conventional methods are generally temperature-dependent, so that, to determine a comparison value, a temperature-compensation calculation is necessary.

In conventional methods for determining the oil viscosity, because the engine is in operation, a large part of the oil medium to be measured is in circulation. Therefore, it is not always possible to sufficiently wet the oil-viscosity measuring sensor, which may result in measuring errors.

SUMMARY OF THE INVENTION

The exemplary method according to the present invention may have the advantage that, as a result of the simultaneous determination of the oil temperature using a temperature sensor that is assigned to the sensor for measuring the oil viscosity, it is possible to reliably record a viscosity-temperature characteristic curve. A further evaluation variable may be available for evaluating the oil condition using the viscosity index that is characterized by the temperature-viscosity curve. In addition, the exemplary method according to the present invention, as a result of measuring the oil viscosity and the oil temperature in the cooling phase of the engine after it has been switched off, may have the advantage that the measurements can be carried out within a relatively large temperature range (assuming ambient temperatures in the area of about 25° C. and operating temperatures of the motor oil in a range of up to about 150° C.). A measuring temperature range of this type occurs during the warm-up phase of the motor oil, although the above-mentioned disadvantages such as insufficient wetting of the measuring sensor(s) may occur as a consequence of the motor being in operation.

The control of the oil-temperature and oil-viscosity measurements as well as the storing and evaluating of the measuring results obtained can be accomplished according to an exemplary embodiment of the present invention by an engine control unit assigned to the engine. This may offer the advantage that, for carrying out the exemplary method according to the present invention, no special control electronics may be necessary, because conventional engine control units are still in operation even during a so-called slowing-down time after the engine is switched off. This slowing-down time can be up to about 30 minutes, so that it may be advantageous to carry out the measurements of oil temperature and oil viscosity in a time interval of up to about 100 minutes, possibly from about 10 minutes to about 30 minutes after the switching-off of the engine. In this manner, numerous measuring values may be produced, which may make possible a sufficiently precise viscosity-temperature characteristic curve for the assessment of the deterioration of the motor oil.

It may also be expedient to assign the evaluation to a computing device that is arranged in the instrument panel, which may result in a further reduction in the components. Alternatively, it may be possible to integrate the evaluation in the engine control unit. Because the oil-viscosity and oil-temperature measuring values may be determined and their subsequent evaluation is carried out after the engine has been turned off, sufficient computing capacity may be present for the evaluation of the measuring values, in contrast to evaluation times while the engine is in operation. In response to the next commencement of travel, the measuring values obtained may be conveyed to the vehicle user by the display device assigned to the evaluating electronics. Because the condition of the motor oil may change only slightly during a single journey, conveying oil-condition information outside of "real-time operation" may be unproblematic.

DETAILED DESCRIPTION

After the engine of a motor vehicle is switched off, the measuring cycle of the exemplary method according to the present invention for the simultaneous determination of the oil-temperature and the oil-viscosity values is initiated by the engine control unit arranged on the engine. In the cooling phase of the engine, a continuous measurement of the relevant variables is carried out in fixed time intervals or as a function of a specific temperature interval of the motor oil.

It is possible to carry out the determination of the oil-viscosity values in response to a cooling-off of the motor oil by about 5° C. The overall interval for the continuous determination of oil temperature and oil viscosity may correspond to the slowing-down time of the engine control unit. During this slowing-down time, the oil-temperature/oil-viscosity values measured are simultaneously stored in an evaluating electronics, and a viscosity index (which may be the determinative variable for assessing the motor oil deterioration), is formed from the corresponding characteristic curve.

If, in the context of the evaluation of the recorded values, it is determined that the deterioration of the motor oil has progressed to the point that a change in motor oil is necessary, then in response to the next engine start, this information may be conveyed to the vehicle user by an appropriate display device.

It may also be possible to record and evaluate measuring values regarding other fluids that are present in the vehicle in the cooling phase of the engine during the slowing-down time of the engine control unit.

What is claimed is:

1. A method for assessing a deterioration of a motor oil for determining a length of an oil-change interval of the motor oil, comprising:

measuring the viscosity of the motor oil by a viscosity sensor at a plurality of times;

assigning to the viscosity sensor a temperature sensor;

measuring the temperature of the motor oil by the temperature sensor at substantially the same times as the plurality of viscosity measurements;

analyzing the plurality of viscosity measurements and the plurality of temperature measurements to obtain an indication of the deterioration of the motor oil; and determining a length of an oil-change interval based on the indication of the deterioration of the motor oil, using evaluating electronics;

wherein the measuring of the oil viscosity and the measuring of the oil temperature occur in a cooling phase of an engine after the engine has been switched off.

2. The method as recited in claim 1, further comprising:

regulating and monitoring, by an engine control device that is assigned to the engine, the measuring of the oil viscosity, the measuring of the oil temperature, and the determining of the length of the oil-change interval.

3. The method as recited in claim 1, wherein the measuring of the oil viscosity and the measuring of the oil temperature are performed in a time interval of about 10 minutes to about 100 minutes after the engine has been switched off.

4. The method as recited in claim 1, wherein the evaluating electronics for determining the length of the oil-change interval is a computing device arranged in an instrument panel, the computing device being driven and monitored by an engine control unit.

5. A method for assessing a deterioration of an oil circulated in a device during use, comprising:

taking a plurality of oil viscosity readings after the device has been switched off and the oil is no longer circulating;

taking a plurality of oil temperature readings at substantially the same times as the oil viscosity readings; and assessing the deterioration of the motor oil based on the oil viscosity readings and the oil temperature readings.

6. The method of claim 5, wherein the oil temperature is elevated during use, and wherein the oil viscosity and oil temperature readings are taken during a cooling phase of the device.

7. The method of claim 6, further comprising:

determining a length of an oil-change interval using evaluating electronics including a display device.

8. The method of claim 7, wherein the device is a motor and the oil is a motor oil.

9. The method of claim 8, wherein measuring of the oil viscosity and oil temperature is performed in a time interval of about 10 minutes to about 100 minutes after the motor has been switched off.

10. A detector for detecting deterioration of oil circulated in a device, comprising:

an oil viscosity sensor configured to measure oil viscosity at a plurality of times after the device has been switched off and the oil is no longer circulating;

a temperature sensor configured to measure oil temperature at substantially the same times as the oil viscosity measurements; and a computing unit configured to assess the deterioration of the motor oil based on the plurality of oil viscosity measurements and the plurality of oil temperature measurements taken after the device has been switched off and the oil is no longer circulating.

11. The detector of claim 10, wherein the oil temperature is elevated during circulation in the device and the detector is configured to take oil viscosity readings and the oil temperature readings during a cooling phase of the device.

12. The detector of claim 11, wherein the computing unit is configured to determine a length of an oil-change interval using evaluating electronics including a display device.

13. The detector of claim 12, wherein the computing unit is controlled and monitored by an engine control unit.

14. The detector of claim 13, wherein the device is a motor and the oil is a motor oil.

15. The detector of claim 10, wherein the detector is configured to take the oil temperature and the oil viscosity readings in a time interval of about 10 minutes to about 100 minutes after the device has been switched off.

* * * * *